United States Patent [19]

Reed

[11] Patent Number: 5,730,976

[45] Date of Patent: *Mar. 24, 1998

[54] METHOD FOR TREATING MACROPHAGE PATHOGEN INFECTIONS BY TGF-B ANTAGONISTS

[75] Inventor: Steven G. Reed, Bellevue, Wash.

[73] Assignee: Corixa Corporation, Seattle, Wash.

[*] Notice: The term of this patent shall not extend beyond the expiration date of Pat. No. 5,543,143.

[21] Appl. No.: 692,667

[22] Filed: Aug. 5, 1996

Related U.S. Application Data

[63] Continuation of Ser. No. 301,216, Sep. 6, 1994, Pat. No. 5,543,143, which is a continuation-in-part of Ser. No. 96,100, Jul. 23, 1993, abandoned, which is a continuation-in-part of Ser. No. 847,441, Mar. 6, 1992, abandoned.

[51] Int. Cl.$^6$ .................. A61K 39/395; A61K 38/18; A61K 38/43; C07K 16/24

[52] U.S. Cl. .................. 424/130.1; 424/142.1; 424/145.1; 424/158.1; 530/388.24; 530/388.23; 530/350; 514/2; 514/8

[58] Field of Search .................. 424/130.1, 145.1, 424/158.1, 142.1; 530/388.24, 388.23, 350; 514/2, 8

[56] References Cited

U.S. PATENT DOCUMENTS 5,543,143  8/1996  Reed .................. 424/130.1

OTHER PUBLICATIONS

Sher, A., et al (Immunological Reviews 127,183), 1992.
Zhou, D., et al., (FASEB J. 5,2582), 1991.
Geissler R. G., et al. (Ann. Hematology 62,151), 1991.
Arteaga et al., "Anti-Transforming Growth Factor (TGF)-β Antibodies Inhibit Breast Cancer Cell Tumorigenicity and Increase Mouse Spleen Natural Killer Cell Activity," *J. Clin. Invest.* 92: 2569-2576, 1993.

*Primary Examiner*—Stephen Walsh
*Assistant Examiner*—Mukul Ranjan
*Attorney, Agent, or Firm*—Seed and Berry LLP

[57] ABSTRACT

There is disclosed a method of treating a mammal infected with a macrophage pathogen comprising administering an effective amount of a TGF-β antagonist. Macrophage pathogens include any pathogenic microorganism that replicates within macrophage cell hosts as their exclusive or primary host cells. TGF-β antagonists include blocking antibodies specific for a human TGF-β, soluble TGF-β receptors, protease inhibitors that inactivate a protease responsible for activating a precursor TGF-β into an active, mature TGF-β, and combinations thereof.

3 Claims, 9 Drawing Sheets

METHOD FOR TREATING MACROPHAGE PATHOGEN INFECTIONS BY TGF-B ANTAGONISTS

CROSS-REFERENCE TO RELATED APPLICATIONS

This application is a continuation of U.S. patent application Ser. No. 08/301,216, filed Sep. 6, 1994, now U.S. Pat. No. 5,543,143; which application is a continuation-in-part of U.S. patent application Ser. No. 08/096,100, filed Jul. 23, 1993, now abandoned; which application is a continuation-in-part of U.S. patent application Ser. No. 07/847,441, filed Mar. 6, 1992, now abandoned.

TECHNICAL FIELD OF THE INVENTION

The present invention relates to a method of activating macrophages/monocytes in an individual infected with a macrophage pathogen, comprising administering an effective amount of a Transforming Growth Factor-β (TGF-β) antagonist.

BACKGROUND OF THE INVENTION

Activated macrophages or monocytes are an important arm of an immune or inflammatory response. These white blood cells ingest microbes, produce and release (intracellularly) reactive oxygen species, and secrete various cytokines that upregulate immune and inflammatory responses of an infected mammal to the microbe or microbes causing the infection. Certain microbes, however, have developed mechanisms to circumvent the anti-microbial activity of activated macrophages/monocytes. Such microbes are referred to as macrophage pathogens, and include any microorganism that replicates or proliferates within host macrophage or monocytic cells as their exclusive or primary host cells.

Examples of macrophage pathogens include Leishmania spp., *Trypanosoma cruzi, Mycobacterium tuberculosis* and *Mycobacterium leprae*, as well as the protozoan *Toxoplasma gondii*. The fungi *Histoplasma capsulatum, Candida albicans, Candida parapsilosis*, and *Cryptococcus neoformans* can also be considered macrophage pathogens. Additional examples include the Rickettsia, for example, *R. prowazekii, R. coronii*, and *R. tsutsugamushi*. Infectious disease in which one or more macrophage pathogen is present can also occur.

One cytokine which is associated with both immune regulation and control of macrophage activation is Transforming Growth Factor-β (TGF-β). This 24 Kd protein is produced by many cells, including B cells, T cells and activated macrophages. TGF-β has been implicated as a mediator of immunosuppression, as inhibiting Interleukin-2 (IL-2) receptor induction, as mediating Interleukin-1 (IL-1) induced thymocyte proliferation, and other activities. In addition, TGF-β has the ability to inhibit cytokine-induced macrophage activation, and to suppress production of reactive oxygen and nitrogen intermediates. Thus, there is a need in the art to determine if TGF-β antagonists will be effective as anti-microbial agents in vivo.

SUMMARY OF THE INVENTION

The present invention relates to a method of treating a mammal infected with a macrophage pathegon, comprising administering an effective amount of a TGF-β antagonist. TGF-β antagonists are pharmaceutical compositions capable of blocking activity of the cytokine TGF-β. Macrophage pathogens are microorganisms that replicate within macrophages as their exclusive or primary host cells. Such pathogens include, for example, Leishmania, Listeria, Mycobacteria, Salmonella, *T. cruzi*, Pneumocystis, and Toxoplasma.

TGF-β antagonists include, for example, blocking (neutralizing) antibodies specific for a human TGF-β, soluble TGF-β receptors, membrane-bound TGF-β receptors, protease inhibitors that inactivate a protease responsible for activating a precursor TGF-β into mature TGF-β, antibodies specific to TGF-β receptors (Types I, II or III) and which prevent TGF-β binding to the receptor, and combinations thereof.

DETAILED DESCRIPTION OF THE INVENTION

Figure 1:
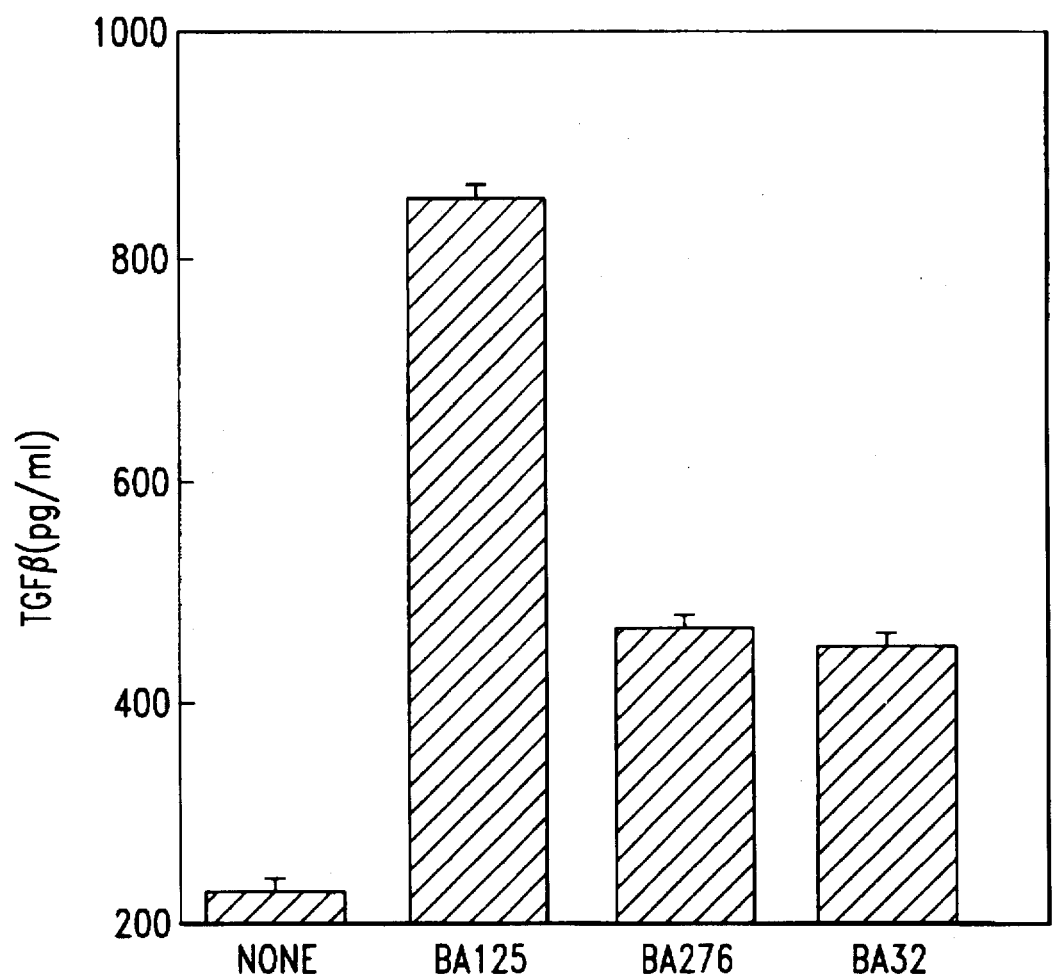
FIG. 1 illustrates a comparison of TGF-β production in vitro induced by Leishmania. Active TGF-β was produced by murine macrophages upon infection with *L. amazonensis*. Data represent the mean plus standard error of the mean of the peak response (obtained 72 hours post-infection) of three different isolates of *L. amazonensis*, compared to uninfected cells. Details of this experiment are presented in Example 1 herein.

The present invention relates to a method of treating a mammal infected with a macrophage pathogen, comprising administering an effective amount of a TGF-β antagonist. The present invention was conceived by the research finding that mice infected with the macrophage pathogen Leishmania can be treated with a blocking monoclonal antibody specific to murine TGF-β. The murine model used is believed by those skilled in the art to provide results that are correlatable to results obtained in various mammalian species, including humans. Moreover, the results of testing done using various in vitro models have demonstrated not only that human and murine macrophage pathogens react similarly to infection by Leishmania, but that other macrophage pathogens also utilize a similar mechanism to deactivate macrophage pathogens, and are susceptible to similar treatments that will allow infected macrophages to resume their activated, anti-microbial role. Moreover, the findings described herein have been subsequently confirmed for other macrophage pathogens.

In the case of Mycobacteria infections, it was found that human macrophages infected with M. avium produced elevated amounts of TGF-β, and that monoclonal antibody to TGF-β was able to synergize with IFN-γ in vitro to inhibit intra-macrophage growth of this organism (Bermudez, J. Immunol. 150:1838, 1993). In other studies, it was found that infection of mouse macrophages with Toxoplasma gondii led to the production of TGF-β, and that exogenous TGF-β could significantly enhance macrophage infection with this pathogen (Gazzinelli et al., reviewed in Sher et al., Immunological Reviews 1992, No. 227, pages183–204). Baldwin et al. also report a role for TGF-β in the intracellular killing of Candida pseudotropicalis by human macrophages (Abstract 84, presented at the 35th Annual Meeting of the American Society of Hematology, 1993).

Thus, the findings described herein, in a predictive animal model, provide data to fully enable the inventive method of treating a mammal infected with a macrophage pathogen, with a pharmaceutical composition comprising a substance with TGF-β antagonist activity. Examples of TGF-β antagonists include antibodies or monoclonal antibodies that are blocking (neutralizing) for human TGF-β, soluble TGF-β receptors, membrane-bound TGF-β receptors, protease inhibitors that inactivate a protease responsible for activating precursor TGF-β into an active, mature TGF-β form, and combinations thereof.

Macrophage Pathogens

Leishmania are obligate intracellular macrophage parasites which cause a variety of human diseases, characterized by visceral, cutaneous, or mucosal lesions. Different species and isolates of Leishmania vary in their ability to infect and replicate in macrophages both in vivo and in vitro. Clinically, infections with L. braziliensis present as single or multiple cutaneous lesions, with a small percentage progressing to a more severe mucosal disease. While the cutaneous lesions may heal spontaneously or respond well to chemotherapy, mucosal lesions are often highly destructive and relatively refractory to treatment. Even if the mucosal lesion cures, there is often spontaneous relapse, perhaps years later.

The course of infection with the protozoa and macrophage pathogen Leishmania is determined, in part, by their early replication in macrophages, the exclusive host cells for these organisms. Although factors contributing to the inhibition or proliferation of Leishmania are not well understood, certain cytokines can influence the course of infection. We have found that Leishmania infection induces production of active TGF-β both in vivo and in vitro, and that TGF-β plays an essential role in determining in vivo resistance and susceptibility to Leishmania infection in an experimental mouse model.

The hemoflagellate protozoan Trypanosoma cruzi (T. cruzi) causes Chagas' disease, a major public health problem in many countries of Latin America. Infection with this parasite may be acute or chronic, and frequently involves development of progressive pathology in tissues of the heart, esophagus and colon. The parasites infect a variety of nucleated cells, including macrophages. In both human and laboratory animals, T. cruzi infection is accompanied by a non-specific immune-suppression mediated by T cells and macrophages. Mechanisms which control parasite replication during the acute and chronic phases and which maintain low but persistent numbers of circulating parasites during the chronic phase are not well understood.

Additional examples of macrophage pathogens include Mycobacterium tuberculosis and Mycobacterium leprae, as well as the protozoan Toxoplasma gondii. The fungi Histoplasma capsulatum, Candida albicans, Candida parapsilosis, and Cryptococcus neoformans can also be considered macrophage pathogens. Certain of the Rickettsia, for example, R. prowazekii, R. coronii, and R. tsutsugamushi are also included, as are combinations of two or more macrophage pathogens.

In addition to infecting humans, many of these macrophage pathogens infect other mammals, which then can serve as a reservoir of infection for humans. For example, domesticated dogs are believed to serve as a major reservoir of Leishmania, while cats are known to carry Toxoplasma. Methods of augmenting a mammals' immune and/or inflammatory response against these macrophage pathogens are thus likely to be useful in other species of mammals than humans.

TGF-β and TGF-β Antagonists

TGF-β is a 24 Kd protein produced by many cells, including B and T lymphocytes and activated macrophages, as well as by many other cell types. Among the effects of TGF-β on the immune system are inhibitions of IL-2- receptor induction, IL-1-induced thymocyte proliferation and blocking of gamma interferon-induced macrophage activation. TGF-β is believed to be involved in a variety of pathological conditions (reviewed in Border and Ruoslahti, *J. Clin. Invest.* 90:1, 1992).

The effects of TGF-β are mediated by the binding of active TGF-β to specific receptors present on cells, followed by transduction of signal to those cells. TGF-β antagonists are defined as molecules that inhibit TGF-β signal transduction. TGF-β antagonists are known in the art. For examples, molecules that bind TGF-β and prevent TGF-β from binding to a TGF-β receptor will act as TGF-β antagonists. Such molecules include neutralizing antibodies to TGF-β, such as those described by Dasch et al. (*J. Immunol.* 142:1536–1541, 1989) and Lucas et al. (*J. Immunol.* 145:1415–1422, 1990). Those skilled in the art recognize various ways in which an antibody derived from one species, for example a mouse, can be engineered in order to be therapeutically useful in a second species, for example a human. Certain of these techniques are briefly reviewed in Harris and Emery, TIBTECH 11:42–44, 1993.

TGF-β is generally secreted as latent precursor consisting of TGF-β non-covalently associated with a protein designated latency-associated protein (LAP; reviewed in Harpel et al., *Prog. Growth Factor Res.* 4:321; 1992). This latent complex requires enzymatic cleavage of carbohydrate groups or transient acidification to release the active cytokine. Purified LAP by itself binds active TGF-β with high affinity to form a latent complex. A DNA encoding a 278 amino acid peptide corresponding to pre-pro-TGF-β, terminating just prior to the mature form of TGF-β and containing a Cys33 to Ser33 substitution has been expressed (Derynck et al., *Nature* 316:701; 1985), and found to bind TGF-β and render it latent.

Soluble forms of TGF-β receptors will also bind TGF-β and prevent binding to membrane-associated TGF-β receptors. TGF-β receptors are described by Wang et al. (*Cell* 67:797–805, 1991) and Lin et al. (*Cell* 68:775–785, 1992). Soluble forms of TGF-β receptors may be prepared by methods that are known in the art. For example, deletion mutants lacking the transmembrane domain of a TGF-β receptor can be prepared, which will express a soluble TGF-β binding protein. Miyazono et al. (*Adv. Immunol.* 55:181; 1994) have recently reviewed TGF-β receptors Other types of TGF-β antagonists are also known in the art. For example, Yamaguchi et al. (*Nature* 346:281–284, 1990) discuss decorin, a small chondroitin-dermatan sulphate proteoglycan that binds TGF-β and modulates the activity of this growth factor. Ohtsuki and Massague (*Mol. Cell. Biol.* 12:261–265, 1992) disclose protein kinase inhibitors that block certain biological activities of TGF-β. *T. cruzi* produces a cysteine protease (cruzain or cruzipain; Eakin et al., *J. Biol. Chem.* 267:7411; 1992) which converts inactive TGF-β precursor into active, mature TGF-β. The design and use of protease inhibitors as drugs is well known in the art (*Design of Enzyme Inhibitors as Drugs*; Sandler and Smith, eds; 1989, Oxford University Press; *Proteinase Inhibitors Medical and Biological Aspects*; Katunuma, Umezawa and Holzer, eds., 1983, Springer-Verlag); thus, inhibitors of cruzain van be prepared and will be useful as TGF-β antagonists.

In vitro and in vivo models

The murine model described is recognized as an appropriate animal model of infectious disease caused by macrophage pathogens by those skilled in the art. Murine models of many other infectious human diseases are known in the art. For example, Sher (*Imm. Rev.* 127:183–204, 1992), discusses murine models of several different human diseases, including acquired immunodeficiency syndrome (AIDS), toxoplasmosis, leishmaniasis, trypanosomiasis, and shistosomiasis. Nathan (in: *Mechanisms of Host Resistance to Infectious Agents, Tumors, and Allografts*, R. M. Steinman and R. J. North, eds., Rockefeller University Press, New York, pp. 165–184, 1986) also reviews the use of mice in the study of various human diseases, and further presents results of studies performed in humans that confirm results first observed in murine models. Rats and/or mice have also been used in animal models of cryptosporidiosis (Meulbroek et al., *Workshop on Pneumocystis, Cryptospridium and Microsporidium* 113S), *Salmonella typhimurium* infections (Hougen et al., APMIS 98:30; 1990), *Mycobacterium avium* infections (Furney et al., *Antimicrobial Agents and Chemotherapy* 34:1629; 1990), and of *Pneumocystis carinii* pneumonia (Boylan and Current, *J. Protozool.* 38:138S; 1991; Soulez et al., *Workshop on Pneumocystis, Cryptospridium and Microsporidium* 123S)

Other species also provide useful animal models. For example, Wyand (*AIDS Res. and Human Retroviruses* 8:349; 1992) discusses the use of SIV-infected Rhesus monkeys for the preclinical evaluation of AIDS drugs and vaccines. Simian and feline models (Gardner, *Antiviral Res.* 15:267; 1991; Stahl-Hennig et al., *AIDS* 4:611; 1990) and murine models (Ruprecht et al., *Cancer Res.* 50:5618s; 1990) have been proposed for evaluating anti-retroviral therapy. Rhesus monkeys have also been used in a model of Chagas' disease (Bonecini-Almeida et al., *Mem. Inst. Osaldo Cruz* 85:163; 1990; Rio de Janeiro). Various non-human primates have been observed to suffer naturally- or experimentally-acquired leprosy (Meyers et al., *Am. J. Trop. Med and Hyg.* 44:24; 1991). Those skilled in the art recognize these and many other possible animal models of disease caused by macrophage pathogens.

Activated macrophages ingest (phagocytose) microbes, produce and release (intracellularly) reactive oxygen species, and secrete various cytokines that upregulate immune and inflammatory responses of the mammal to the microbe or microbes. Activation (or re-activation) of macrophages is confirmed in vitro by various means involving measuring one or more of these activities.

For example, activated macrophages produce and secrete various cytokines, including Interleukin-6 (IL-6), Interleukin-1α and β (IL-1α, IL-1β), Tumor Necrosis Factor α, (TNF-α), Interleukin-8 (IL-8), Macrophage Inhibitory Peptide-1α (MIP-1α), Macrophage Inhibitory Peptide-1β, MIP-1β, and growth regulatory protein GRO. Activation may thus be determined by measuring the secretion of one or more of these cytokines, or by analyzing levels of transcription of mRNA for one or more of these cytokines. Moreover, as described herein in the Examples, macrophages can be observed in vitro (after activation either in vitro or in vivo) to determine effective phagocytosis of microbe organisms and/or production of TGF-β. Methods of measuring the production and release of reactive oxygen species are well-known in the art.

It is thus a matter of routine experimentation to determine if a TGF-β antagonist facilitates activation (or re-activation) of macrophages/monocytes after incubation of the macrophages with the TGF-β antagonist in vitro. Similarly, it is also a matte of routine experimentation to remove macrophages from a mammal that has been treated with a TGF-β antagonist, and determining if these macrophages are activated.

Administration of TGF-β Antagonists

The present invention provides methods of using therapeutic compositions comprising an effective amount of a TGF-β antagonist and a suitable diluent and carrier, and methods for regulating an immune or inflammatory response. The use of TGF-β antagonists in conjunction with soluble cytokine receptors or cytokines, or other immunoregulatory molecules is also contemplated.

For therapeutic use, purified TGF-β antagonist is administered to a patient, preferably a human, for treatment in a manner appropriate to the indication. Thus, for example, TGF-β antagonist compositions administered to augment immune and/or inflammatory function of macrophages can be given by bolus injection, continuous infusion, sustained release from implants, or other suitable technique. Typically, a therapeutic agent will be administered in the form of a composition comprising purified TGF-β antagonist in conjunction with physiologically acceptable carriers, excipients or diluents. Such carriers will be nontoxic to recipients at the dosages and concentrations employed.

Ordinarily, the preparation of such TGF-β antagonist compositions entails combining the TGF-β antagonist with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents.

Appropriate dosages can be determined in trials, first in an appropriate animal model, and subsequently in the species to be treated. The amount and frequency of administration will depend, of course, on such factors as the nature and severity of the indication being treated, the desired response, the condition of the individual being treated, and so forth. The appropriate dosages are within the range of about 10 ng/kg/day to about 100 µg/kg/day each or in combination. Preferably a dose of 100 ng/kg/day to about 1000 ng/kg/day for 1-20 days can be expected to induce an appropriate biological effect. Alternatively, bolus injections of from about 1 µg/kg/day to about 100 µg/kg/day can be given at approximately 4-day intervals to exert antimicrobial effects via augmentation of immune and/or inflammatory responses mediated by macrophages/monocytes.

Association of TGF-β with Leishmaniasis

I first investigated whether Leishmania infection may influence the production of TGF-β, and thus potentially use this mechanism to survive and proliferate in macrophages. Using a sensitive bioassay, I found (in vitro) that infection of normal mouse peritoneal macrophages with L. amazonensis led to production of biologically active TGF-β 72 hours following infection. These data are shown in FIG. 1. The study was conducted by obtaining peritoneal macrophages from normal BALB/c mice after thioglycolate stimulation. The macrophages were plated at a concentration of $10^6$ cells/well in a 24-well plate. Non-adherent cells were washed off the plate. The remaining adherent cells were infected with $3\times10^6$ stationary-phase L. amazonensis promastigotes per well for three hours. Extracellular parasites were removed and cells were cultured for another 72 hours in a humid atmosphere of 5% $CO_2$ at 37° C. TGF-β was assayed using a CCL64 cell line technique as described in Silva et al., J. Exp. Med. 174:539, 1991.

There is increased active TGF-β in supernatants of Leishmania infected macrophages. Although latent TGF-β may be produced by uninfected macrophages, the finding of increased levels of TGF-β in culture supernatants of infected macrophages appears to indicate one mechanism by which Leishmania evade host defense by macrophages. Therefore, these data provide an important understanding regarding pathogenesis of infection of macrophage pathogens.

The potential role of TGF-β during infection, in vivo, of a macrophage pathogen was investigated. Leishmania lesions were examined using a murine TGF-β-specific monoclonal antibody. There was local TGF-β production in mouse footpads following Leishmania infection but there was no detectable TGF-β in uninfected footpads of the same mouse. Therefore, increased TGF-β production was associated with Leishmania infection both in vitro and in vivo.

Figure 2A:
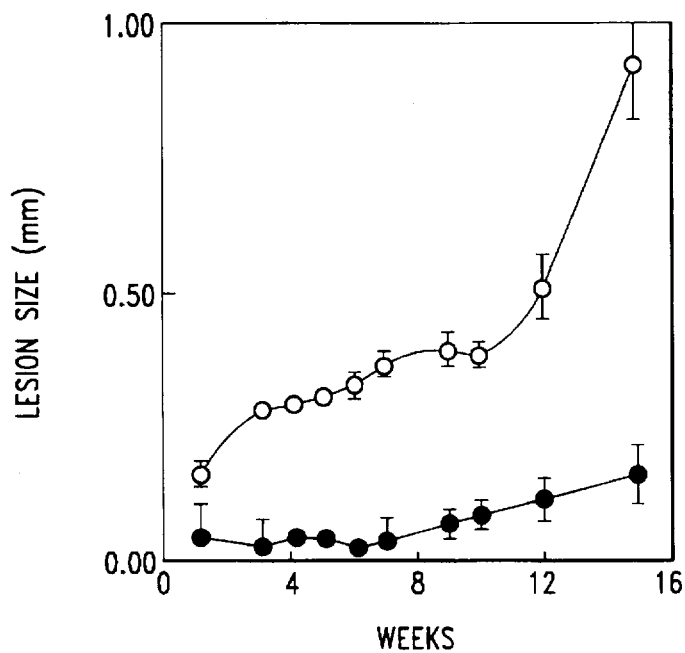
FIGS. 2A and 2B show in vivo effects of TGF-β on the course of cutaneous Leishmaniasis. In panel A, C57BL/6 mice were infected with *L. amazonensis*. TGF-β was injected at 24 hours and at 6, 7, 8 and 9 weeks post infection (open circles). Control animals were injected similarly and at the same time periods with the same amount of saline (close circles). In panel B, BALB/c mice were infected with *L. braziliensis* and recombinant TGF-β was injected subcutaneously into the lesion at 24 hours and at weeks 1, 2, 3, 5, 12, and 13 post infection (open circles). Saline treated controls are shown with closed circles.
Figure 2B:
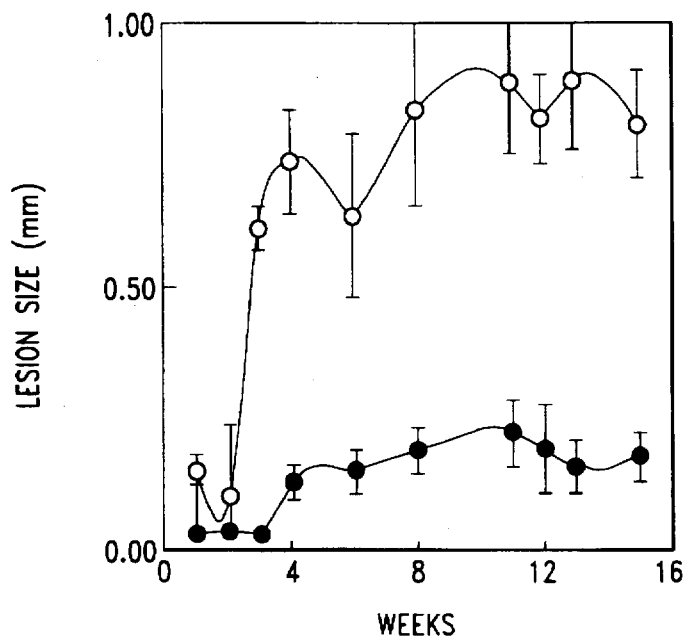

Leishmania resistant C57BL/6 mice will normally heal after Leishmania infections. When such mice were infected with Leishmania, and treated with recombinant TGF-β, the TGF-β treated mice developed large, non-healing lesions (FIG. 2). These data indicate that TGF-β is able to reverse genetic resistance to Leishmaniasis in C57BL/6 mice.

TGF-β also influences infection with L. braziliensis. This parasite does not produce lesions even in BALB/c mice, which are susceptible to infection with other Leishmania species. However, TGF-β treatment led to replication of L. braziliensis and to production of lesions in BALB/c mice (FIG. 2B). When the lesions in the BALB/c mice were investigated histologically, lesions from saline-treated animals were composed of predominately lymphocytic infiltrate, whereas lesions from TGF-β-treated BALB/c mice exhibited a large number of heavily vacuolated and parasitized macrophages among the lymphocytes. Therefore, local administration of TGF-β led to production of acute disease in two different animal models of resistance.

In view of the finding that TGF-β was increased during Leishmania infection and that exogenously-administered recombinant TGF-β could produce exacerbated infections in resistant mice, I investigated whether endogenously-produced TGF-β influenced Leishmania infection in vivo. Highly susceptible BALB/c mice were treated with a neutralizing antibody specific for murine TGF-β during the course of infection with *L. amazonensis*. Control mice were similarly injected with an irrelevant immunoglobulin. In vivo treatment with anti-TGF-β arrested development of lesions resulting from *L. amazonensis* infection in susceptible BALB/c mice (FIG. 3). Inhibition of lesion development was noted by the 5th week post-infection and was maintained thereafter. Therefore, endogenous TGF-β production was directly associated with susceptibility to a macrophage pathogen such as Leishmania. Moreover, anti-TGF-β antibody is a TGF-β antagonist that will have similar biological and pharmacological properties to other TGF-β antagonists, such as other blocking monoclonal antibodies specific for a human TGF-β, soluble TGF-β receptors that bind and inactivate active TGF-β, and protease inhibitors that inactivate a protease responsible for activating a precursor TGF-β into an active, mature TGF-β.

Production of active TGF-β requires infection by live macrophage pathogens or other parasites, and represents an important parasite virulence mechanism. In addition, exogenously-administered TGF-β was shown to have profound effects on the course of macrophage parasite infection. Genetically resistant mice became susceptible to macrophage parasite infection following TGF-β treatment, and avirulent Leishmania produced disease in conjunction with TGF-β. In the aggregate, these data demonstrate a unique role for TGF-β in mediating resistance and susceptibility to a parasitic protozoan, and represent an important mechanism by which macrophage pathogens avoid destruction by host macrophages. The data further predict and enable the full scope of the claimed invention.

EXAMPLE 1

This example illustrates that active TGF-β is produced in vitro by macrophages infected with Leishmania. Macrophages are both host cells for Leishmania and other macrophage parasites and important producers of the cytokine TGF-β. I analyzed the production of TGF-β during in vitro infection of peritoneal macrophages from normal mice. Thioglycolate-stimulated mouse peritoneal macrophages were plated in 24-well plates at $5\times10^5$ cells/well in RPMI1640 supplemented with antibiotics, glutamine, and 10% heat-inactivated fetal calf serum. After three days in culture, macrophages were infected with stationary-phase *L. braziliensis* promastigotes ($2.5\times10^6$ parasites/well) for three hours. Extracellular parasites were removed by extensive washing with wash culture medium, followed by further incubation for up to 72 hours. Cell-free supernatants were collected at 24, 48, or 72 hours after infection. Replicate monolayers were washed with phosphate buffered saline (PBS), fixed in acetone-methanol, and stained with Giemsa. The percentage of infected macrophages, and the number of amastigotes per 100 macrophages were determined by microscopic examination as described in Reed et al., *J. Exp. Med.* 166:1734, 1987.

TGF-β was assayed for presence and activity by taking supernatants from uninfected and Leishmania-infected macrophage cultures and assaying for TGF-β activity using CCL-64 mink lung epithelial cells as described in Ranchalis et al., *Biochem. Biophys. Res. Comm.* 148:783, 1987. Cells were plated at $10^5$ cells/well into 96-well microtiter plates for one hour at 37° C. in volume of 100 µl of DMEM (Dulbecco's Minimal Essential Media) containing 1% heat-inactivated fetal calf serum. After one hour, TGF-β standards (ranging in concentration from 2 ng to 0.00049 ng) or test supernatants were added at appropriate dilutions to a final volume of 200 µl/well. The standards were diluted by 2× serial dilutions in DMEM containing 10% heat-inactivated fetal calf serum. The cultures were incubated for 22 hours at 37° C. and tritiated ($^3$H) thyroidine was added during the final four hours at a concentration of 0.25 µCi/well. The plates were placed in a –70° C. freezer for at least one hour, thawed, and harvested onto glass filter fibers. Radioactivity was determined by liquid scintillation counting.

TGF-β released in its latent or precursor form will not inhibit CCL-64 cell cultures (Twardzik et al., in *Transforming Growth Factors-Chemistry, Biology, and Therapeutics*, Ann. N.Y. Acad. Sci. 593:276, 1990). Hydrochloric acid (1N) was added to each culture supernatant to adjust the pH to 3.0–3.5 for 10 minutes at room temperature and immediately neutralized to pH 7.0–7.6 by adding 1N NaOH. The concentration of TGF-β in each sample was determined by comparison with a curve generated from the TGF-β standards. A sample regression curve was computed using a Microsoft GB STAT® program.

Figure 4:
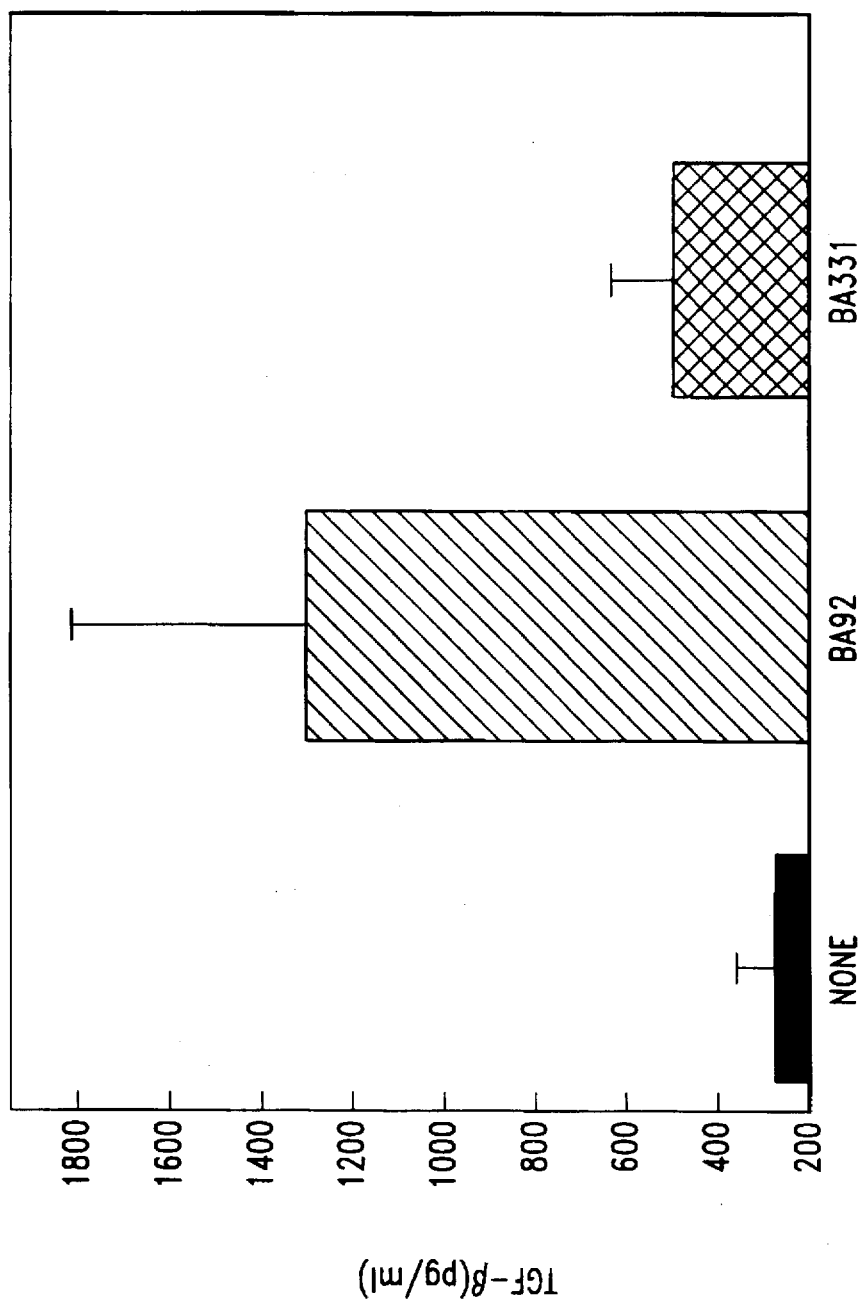
FIG. 4 is a graph showing production of active TGF-β by Leishmania-infected macrophages. Cultures of mouse peritoneal macrophages were infected with *L. braziliensis* (BA-92 or BA-331) and supernatants were collected three days later. Data are shown as the mean plus standard error of the mean from triplicate cultures.

The production of TGF-β in the supernatant of infected macrophages was determined at several time points after infection. Two interesting observations came from these experiments. The first was that biologically active TGF-β was produced by mouse peritoneal macrophages following in vitro infection with Leishmania (FIG. 4). The second was that the levels of TGF-β induced differed between two individual isolates of *L. braziliensis* (BA-92 and BA-331).

EXAMPLE 2

Figure 5:
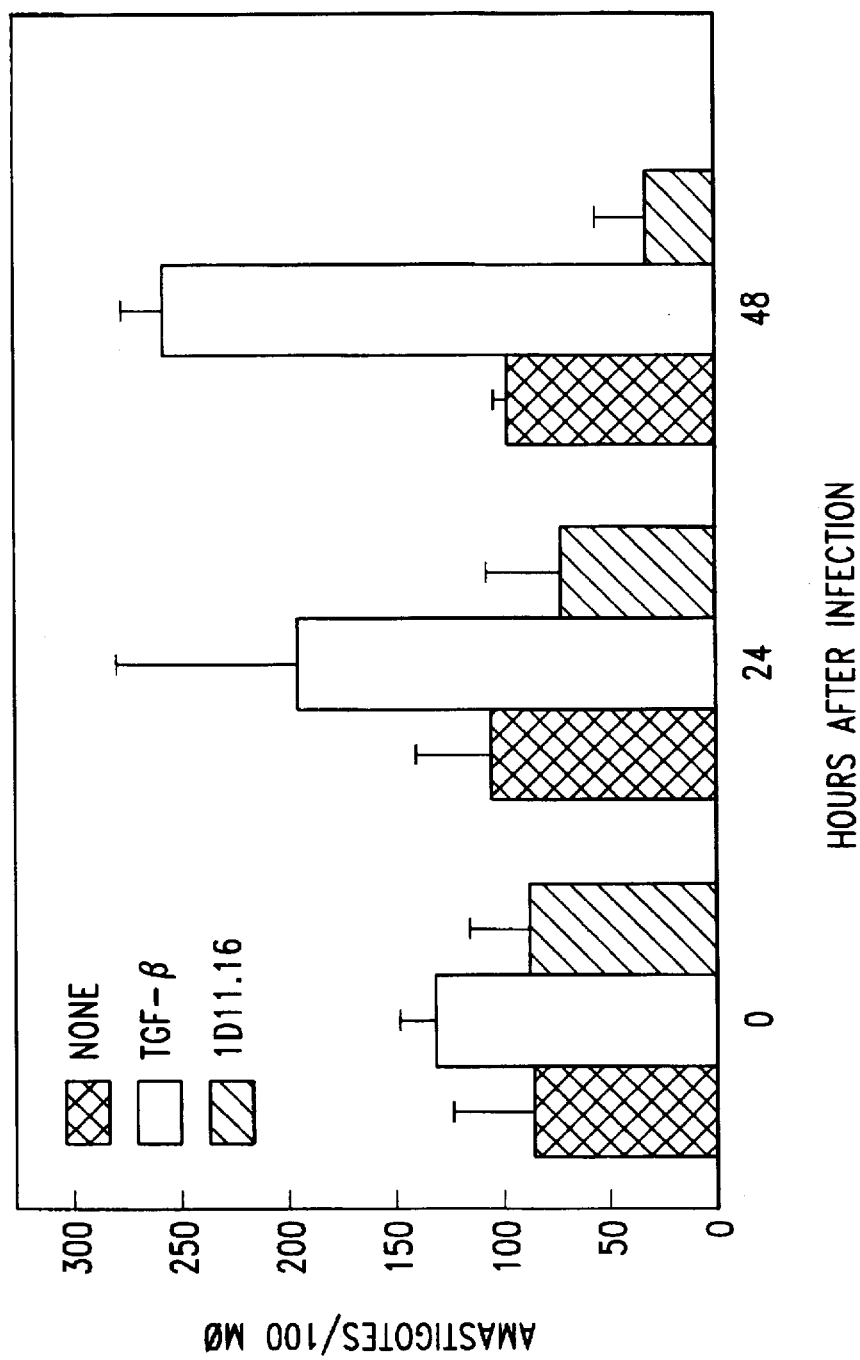
FIG. 5 shows a comparison of TGF-β or a TGF-β antagonist (monoclonal antibody 1D11.16) on in vitro replication of Leishmania in mouse peritoneal macrophages infected with BA-92 and cultured with 2 ng/ml TGF-β (open bars), 200 μg/ml of 1D11.16 (hatched bars) 24 hours before and continuously after infection, or in medium alone (control bars). The numbers of intracellular parasites were determined at 2, 24, and 48 hours after infection.

This example illustrates the effect of TGF-β to exacerbate in vitro infection by *L. braziliensis*. In vitro infection of mouse macrophages by *L. braziliensis* is characterized by static numbers of intracellular parasites. However, when macrophages were treated with recombinant TGF-β prior to infection, a progressive increase in numbers of intracellular amastigotes occurred (FIG. 5). Therefore, explanted macrophages were capable of limiting the intracellular replication of Leishmania, and the mechanism responsible for this control was inhibited by exogenous TGF-β. Regulation of intracellular parasite replication was resisted due to progressive reduction of amastigotes in macrophages treated with a neutralizing monoclonal antibody (mAb) specific for TGF-β. This observation suggests a role for Leishmania-induced TGF-β in the persistence of intracellular macrophage parasites.

EXAMPLE 3

This example illustrates the exacerbation of in vivo Leishmania infection by TGF-β. In examples 1 and 2, in vitro observations suggested a differential ability of Leishmania isolates to induce active TGF-β production as well as a role for TGF-β in control of Leishmania infection. This example illustrates in vivo experiments in which two *L. braziliensis* isolates were used to infect mice with and without administering TGF-β.

BALB/c mice (Jackson Laboratories, Bar Harbor, Me.) were infected in the left hind footpad with $5\times10^6$ stationary-phase promastigotes of Leishmania in 25 µl of saline. The parasites were resuspended in saline containing 40 µg/ml rTGF-β (1 µg/mouse). Recombinant TGF-β treatments were at doses of 1 µg/mouse injected into each infected footpad. Control mice were injected with the same volume of saline. Lesion progression was evaluated during the course of infection by measuring footpad thickness with a dial gauge caliper (C. Starret, Athol, Mass.) and expressed as lesion size in mm (infected footpad thickness minus uninfected contralateral footpad thickness). At different periods of time after infection, animals were sacrificed, infected footpads were removed, fixed in 10% buffered formalin, processed and stained with hematoxylin and eosin.

Figure 6:
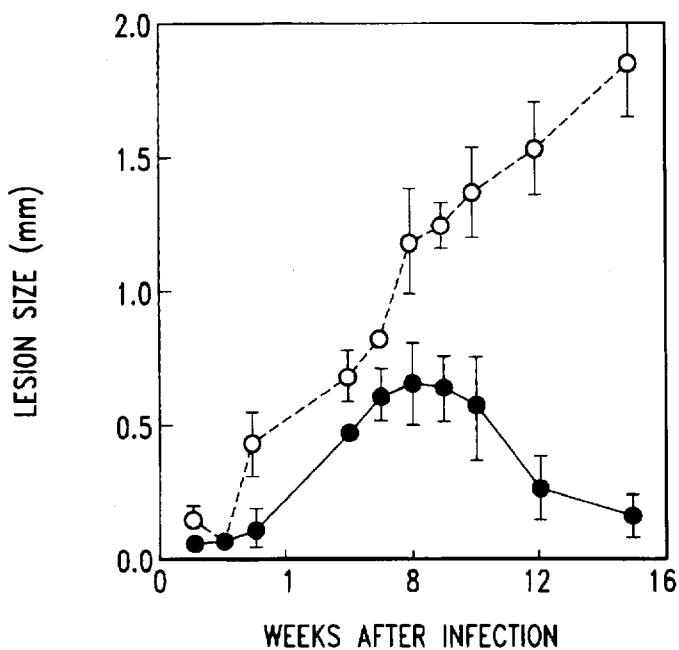
FIG. 6 shows the effects of exogenous TGF-β on the course of *L. braziliensis* infections in BALB/c mice. Infections were made with BA-92 ($5 \times 10^6$ stationary-phase promastigotes) diluted in control saline or in saline containing TGF-β at 40 μg/ml, for a total dose of 1 μg/mouse. Treatments were followed with TGF-β (1 μg/dose, open circles) or saline (closed circles) injected into the infected footpad one time per week for ten weeks.
Figure 7:
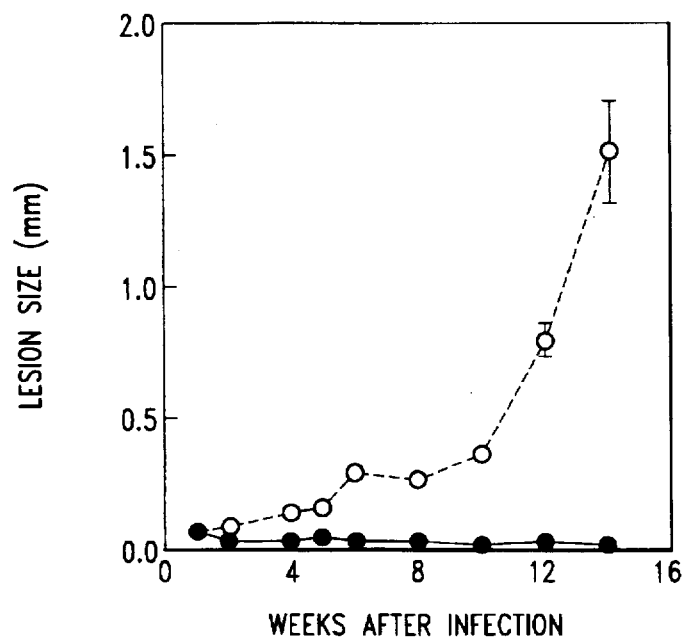
FIG. 7 shows an experiment designed similarly to FIG. 6 except the BALB/c mice were infected with BA-331 instead of BA-92 in FIG. 6.
Figure 8:
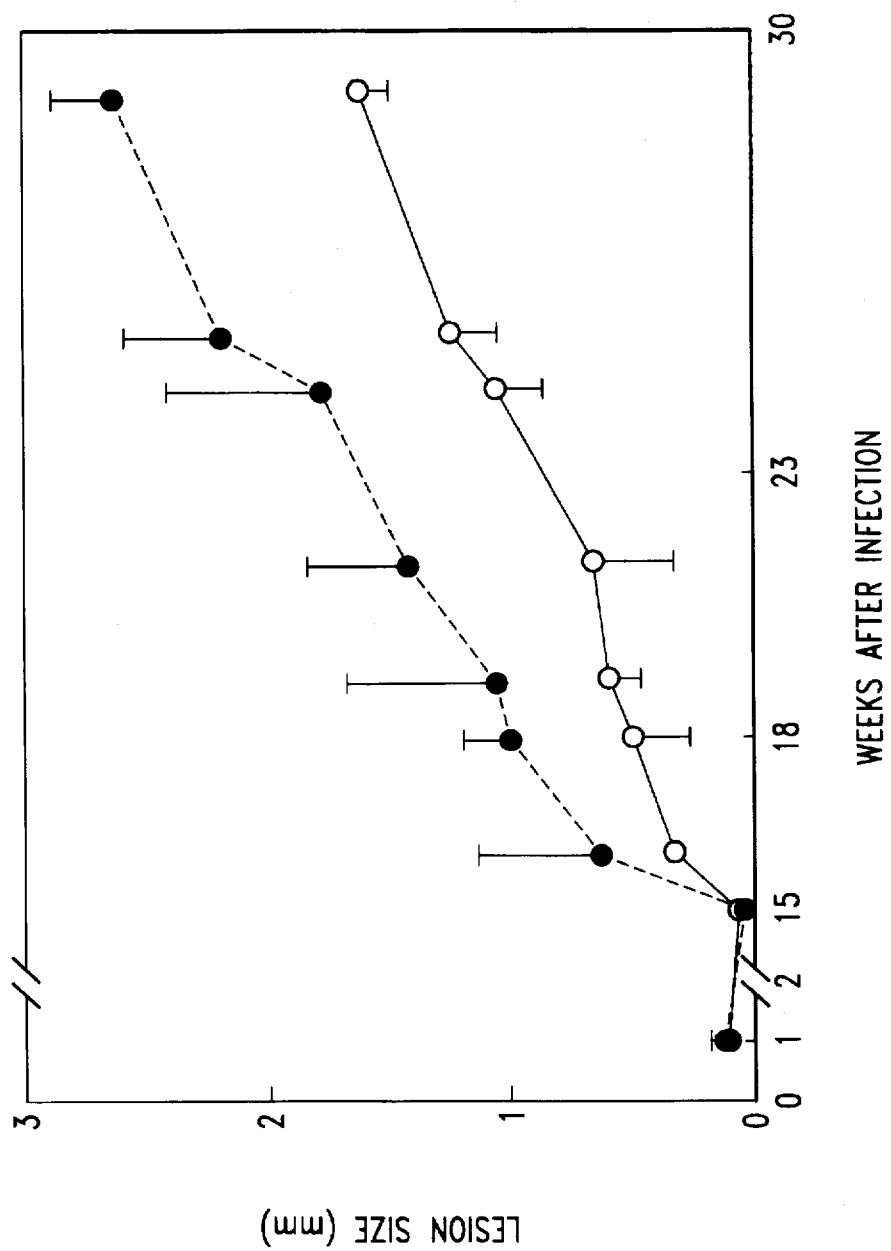
FIG. 8 shows the effect of TGF-β on a previous infection with L. braziliensis. BALB/c mice were infected with either BA-92 (close circles) or BA-331 (open circles) and maintained without treatment for 15 weeks. The mice were then treated with TGF-β (1 μg/injection) or saline for a three week period for three injections per week. Saline-injected controlled mice (triangles) did not develop lesions.

Each isolate of *L. braziliensis* produced characteristic self-limited infections in saline-treated mice (FIGS. 6 and 7). There was a direct correlation seen between lesion size and TGF-β levels induced by the two parasite isolates. Thus, BA-331 was a relatively weak inducer of TGF-β in vitro and produced no measurable lesion, while BA-92 induced measurable but self-limiting lesions as well as significantly higher in vitro levels of TGF-β. These data suggest a role for TGF-β production in Leishmania infectivity and/or intracellular replication in vivo.

Exogenous TGF-β was administered to groups of mice infected with either of these two *L. braziliensis* isolates. Recombinant TGF-β treatment led to a dramatic increase in mean lesion size in all mice (FIGS. 6 and 7). Histologically, the lesions were characterized by large numbers of heavily parasitized macrophages. The differences between recombinant TGF-β-treated and saline-treated mice were greatest in those mice infected with BA-331, which produced measurable lesions only in the presence of TGF-β (FIG. 6). By inducing or exacerbating lesions in *L. braziliensis* infected mice, the role for TGF-β in the pathogenesis of Leishmaniasis was established.

EXAMPLE 4

This example illustrates activation of latent *L. braziliensis* infections by administration of exogenous TGF-β. *L. braziliensis* infection in intact mice is characterized by transient or no lesion development as illustrated in FIG. 6. To determine whether parasites persisted following infection and whether recombinant TGF-β could influence prior infections, BALB/c mice were treated with recombinant TGF-β for a three week period, beginning 15 weeks after initial infection. When recombinant TGF-β was administered there were no visible lesions present characteristic of disease. Animals were treated with recombinant TGF-β (1 μg/mice/dose) or saline, three times a week during a three week period. In both groups, injection of recombinant TGF-β but not saline, led to lesion development that was detected two to three weeks after initiation of treatments (FIG. 8). Even though TGF-β treatment was continued for only three weeks, progressive lesion growth continued throughout a 15 week observation period. Saline treated mice exhibited no change in lesion size. These data illustrate that persistent latency of *L. braziliensis* infection in mice and further demonstrate the ability of TGF-β to mediate disease resistance and susceptibility.

EXAMPLE 5

This example illustrates a protective effect caused by an anti-TGF-β monoclonal antibody as a TGF-β antagonist on the course of cutaneous Leishmaniasis. Mice were infected with *L. amazonensis* as previously described. Four hours after infection, the mice were injected with 1D11.16 (anti-murine TGF-β monoclonal antibody or a similar amount of an irrelevant antibody (isotype-matched myeloma protein). Both antibodies were injected subcutaneously at the lesion site at a volume of 30 µl containing 80 µg/per dose of 1D11.16 or control. Foot lesion growth was measured with a dial caliper to assess the effectiveness of treatment.

Figure 3A:
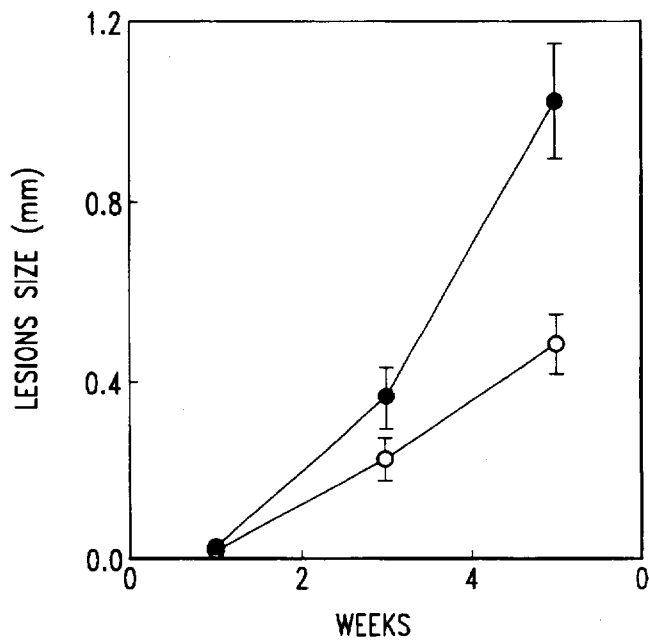
FIGS. 3A and 3B illustrates a protective effect caused by an anti-TGF-β monoclonal antibody as a TGF-β antagonist on the course of cutaneous Leishmaniasis. Panel A describes BALB/c mice infected with *L. amazonensis* and treated six times (three times per week during the first two weeks post-infection) with 1D11.16 (anti-murine TGF-β monoclonal antibody, open circles) or a similar amount of an irrelevant antibody (closed circles). Both antibodies were injected subcutaneously at the lesion site at a volume of 30 μl. Panel B shows data obtained with BALB/c mice infected with *L. amazonensis*. During the first three week post-infection period, mice were treated three times per week with 80 μg/per dose of 1D11.16 or control saline as in Panel A.
Figure 3B:
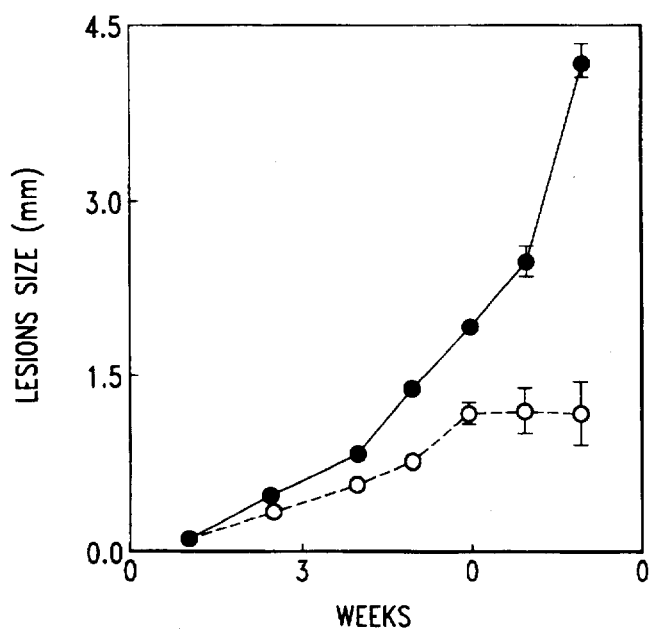

The results are presented in FIG. 3. Panel A illustrates results obtained with BALB/c mice infected with *L. amazonensis* and treated six times (three times per week during the first two weeks post-infection). Panel B shows data obtained with BALB/c mice infected with *L. amazonensis* and treated three times per week as in Panel A during a three week post-infection period. Both treatment regimes resulted in decreased foot lesion growth, indicating the treatment with a TGF-β antagonist is effective at reversing the potent effects of TGF-β on cellular immune responses in vivo.

EXAMPLE 6

Figure 9:
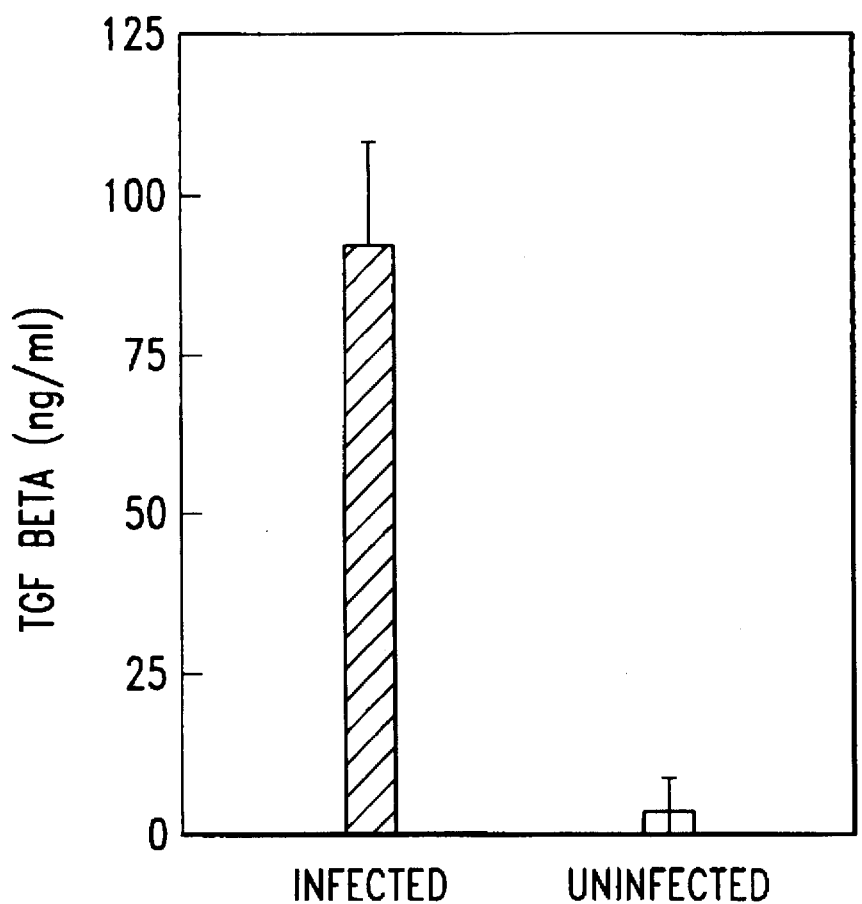
FIG. 9 shows the production of active TGF-β by human monocytes infected with T. cruzi compared to uninfected monocytes.

This example illustrates the production of active TGF-β by human monocytes infected with *T. cruzi*. Human monocytes were obtained from healthy adults using standard methods for isolating monocytes from peripheral blood. The monocytes ($5\times10^5$/ml) were infected with *T. cruzi* trypomastigotes at a multiplicity of infection of 2 parasites per monocyte. The amount of TGF-β in the supernatant fluid was determined using the CCL64 cell inhibition assay described previously, at 48 hours after infection. The results of this experiment, which are presented in FIG. 9, demonstrate that *T. cruzi*-infected human monocytes produce significant levels of TGF-β, thus implicating TGF-β in suppressing the cellular immune response in *T. cruzi* infection.

EXAMPLE 7

Figure 10:
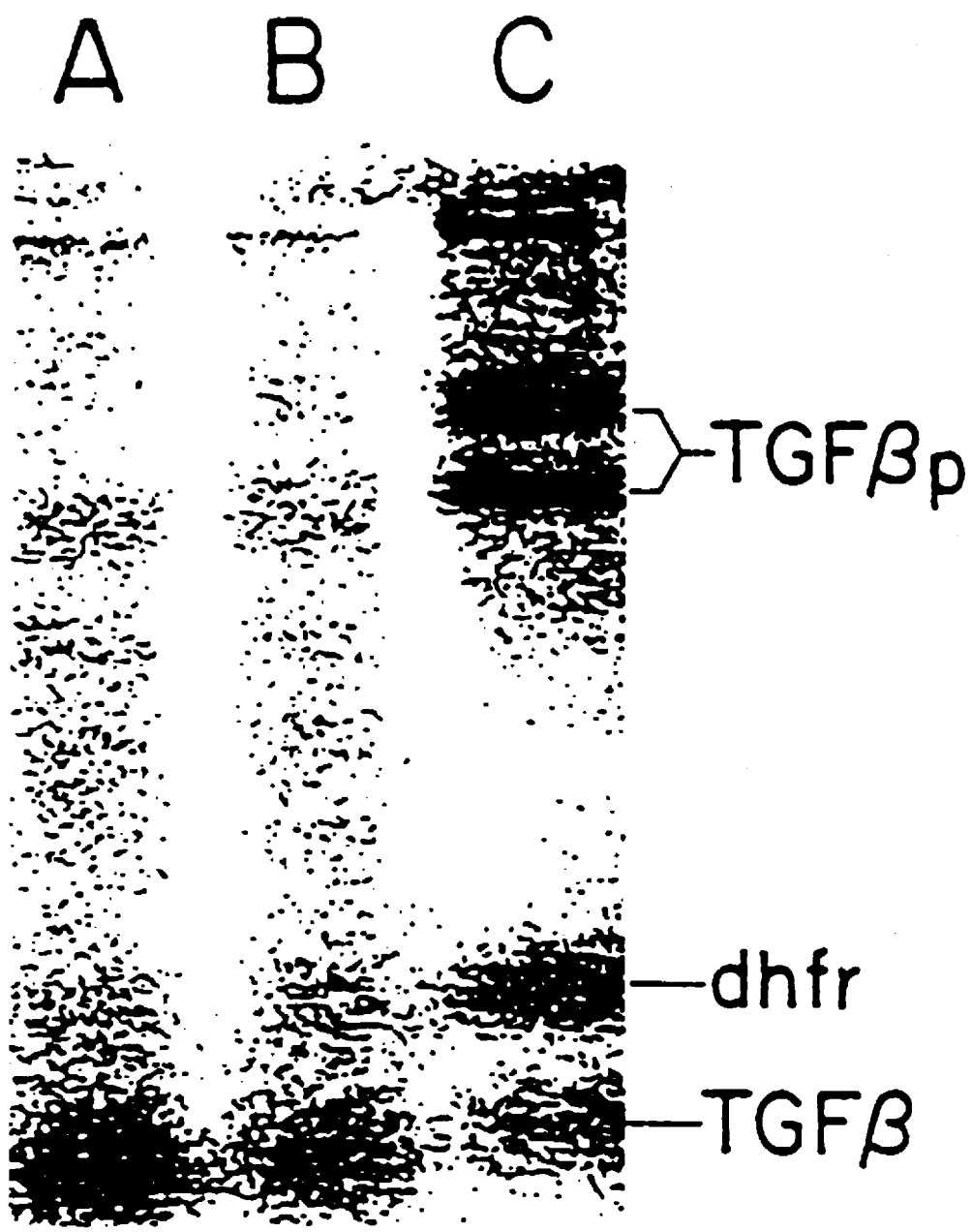
FIG. 10 shows the ability of a T. cruzi enzyme (cruzain) to process TGF-β precursor into mature TGF-β. Precursor TGF-β migrates as a doublet of approximately 45–55 Kd (lane c). Treatment with either native or recombinant cruzain destroyed this doublet, and led to an accumulation of mature TGF-β, which migrates as a protein of approximately 12 Kd (lane a, native cruzain; lane b, recombinant cruzain).

This example illustrates the ability of a *T. cruzi* enzyme to process TGF-β precursor into mature TGF-β. *T. cruzi* is known to produce a cysteine protease, which is referred to as cruzain or cruzipain (Eakin et al., *J. Biol. Chem.* 267:7411; 1992)). To investigate the effects of this enzyme on latent TGF-β, radiolabeled TGF-β (10,000 cpm; Bristol-Myers Squibb Research Institute, Seattle, Wash., U.S.A.) was incubated with 1 µg of purified native cruzain (purified as described in Scharfstein et al., *J. Immunol.* 137:1336; 1986), or with recombinant cruzain (obtained from Dr. James McKerrow, Department of Pathology, UCSF, San Francisco, Calif., U.S.A.) for 30 minutes at 37° C. The samples were then analyzed by SDS-PAGE. The results are presented in FIG. 10. Precursor TGF-β migrates as a doublet of approximately 45–55 Kd (lane c). Treatment with either native or recombinant cruzain destroyed this doublet, and led to an accumulation of mature TGF-β, which migrates as a protein of approximately 12 Kd, as illustrated in lanes a (native cruzain) and b (recombinant cruzain).

EXAMPLE 8

This example illustrates inhibition of the production of active TGF-β by human mononuclear cells infected with *T. cruzi*. Human peripheral blood mononuclear cells (PBMC) were obtained from healthy adults using standard methods for isolating PBMC. The PBMC ($1\times10^6$/ml) were infected with *T. cruzi* trypomastigotes at a multiplicity of infection of 1 parasite per cell. Various TGF-β antagonists were added two hours after infection. Antibody 1D11.16 (described previously; obtained from Celtrix, Palo Alto, Calif.) was added at a concentration of 1 µg/ml; Interleukin-7 (IL-7; Immunex Corporation, Seattle Wash.) at 10 ng/ml; soluble Type II TGF-β1 receptor (sTGFR-II; R&D Systems, Minneapolis, Minn.) at 10 µg/ml; and latency-associated peptide (LAP; R&D Systems, Minneapolis, Minn.) at 10 µg/ml. A control cytokine (IL-15; Immunex Corporation, Seattle, Wash.) was also used. The amount of TGF-β in the supernatant fluid was determined using the CCL64 cell inhibition assay described previously, at 48 hours after infection. The results of this experiment are presented in Table 1.

TABLE 1

| Inhibition of Production of TGF-β | |
|---|---|
| TGF-β Antagonist | TGF-β (ng/ml) |
| Uninfected PBMC | 0 |
| *T. cruzi* alone | 300 |
| *T. cruzi* + 1D11.16 | 10 |
| *T. cruzi* + IL-7 | 0 |
| *T. cruzi* + sTGFR-II | 30 |
| *T. cruzi* + LAP | 36 |
| *T. cruzi* + IL-15 | 320 |

These results confirm that *T. cruzi*-infected human PBMC produce significant levels of TGF-β, and clearly demonstrate that various TGF-β antagonists are effective at inhibiting the production of biologically active TGF-β. The various TGF-β antagonists tested in this in vitro assay are expected to be effective in vivo, as is antibody 1D11.16 (see Example 5). Additional TGF-β antagonists can be tested for effectiveness in vitro using this assay as well.

The data presented herein support the broad applicability of TGF-β antagonists in treating infectious disease caused by macrophage pathogens. As demonstrated both in vitro and in vivo, TGF-β antagonists reverse the deactivation of macrophages/monocytes that macrophage pathogens utilize to render this critical aspect of an immune/inflammatory response ineffective.

I claim:

1. A method of treating a mammal afflicted with a disease associated with a macrophage pathogen, comprising:

administering to the mammal an effective amount of a transforming growth factor-β (TGF-β) antagonist to activate macrophages, wherein the TGF-β antagonist is administered in a pharmaceutically acceptable carrier.

2. The method of claim 1, wherein the TGF-β antagonist is selected from the group consisting of neutralizing monoclonal antibodies specific for TGF-β, protease inhibitors that inactivate a protease responsible for activating a precursor TGF-β into a mature TGF-β, soluble TGF-β receptors, and combinations thereof.

3. The method of claim 1, wherein the macrophage pathogen is selected from the group consisting of: bacteria, yeast, fungi, viruses, protozoa, Rickettsia and combinations thereof.

* * * * *